(12) United States Patent
Weng et al.

(10) Patent No.: US 11,150,191 B2
(45) Date of Patent: Oct. 19, 2021

(54) AUTOMATIC, REAL-TIME SURFACE-ENHANCED RAMAN SCATTERING (SERS) ANALYSIS

(71) Applicant: The Board of Regents of the University of Oklahoma, Norman, OK (US)

(72) Inventors: Binbin Weng, Norman, OK (US); Mark A. Nanny, Norman, OK (US); Joseph M. Suflita, Norman, OK (US); Rouzbeh Ghanbarnezhad Moghanloo, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 16/963,792

(22) PCT Filed: Feb. 28, 2020

(86) PCT No.: PCT/US2020/020454
§ 371 (c)(1),
(2) Date: Jul. 21, 2020

(87) PCT Pub. No.: WO2020/180710
PCT Pub. Date: Sep. 10, 2020

(65) Prior Publication Data
US 2021/0088448 A1 Mar. 25, 2021

Related U.S. Application Data

(60) Provisional application No. 62/812,629, filed on Mar. 1, 2019.

(51) Int. Cl.
*G01N 21/65* (2006.01)
*G01N 21/94* (2006.01)
(Continued)

(52) U.S. Cl.
CPC ....... *G01N 21/658* (2013.01); *G01N 21/0303* (2013.01); *G01N 21/05* (2013.01);
(Continued)

(58) Field of Classification Search
CPC .. G01N 21/658; G01N 21/0303; G01N 21/05; G01N 21/94; G01N 33/18;
(Continued)

(56) References Cited

U.S. PATENT DOCUMENTS 7,267,948 B2    9/2007  Vo-Dinh
7,483,130 B2 *  1/2009  Baumberg ........... G01N 21/658
                                                         356/301

(Continued)

FOREIGN PATENT DOCUMENTS

WO    2018132564 A1    7/2018

OTHER PUBLICATIONS

Hemati, Tahere, et al.; "Theoretical Study of Leaky-Mode Resonant Gratings for Improving the Absorption Efficiency of the Uncooled Mid-Infrared Photodetectors"; J. Appl. Phys. vol. 124; Aug. 6, 2018; 7 pages.

(Continued)

*Primary Examiner* — Jamil Ahmed
(74) *Attorney, Agent, or Firm* — Conley Rose, P. C.; Grant Rodolph; Jonathan K. Polk

(57) ABSTRACT

An apparatus comprises: a photonic cavity; a substrate comprising a waveguide layer, wherein the waveguide layer comprises waveguides configured to direct light towards the photonic cavity; and a wafer comprising: a top side, and a nanowire array affixed to the top side. A method of performing a surface-enhanced Raman scattering (SERS) analysis, the method comprises: directing, using a waveguide layer of a SERS device, an incident light towards a photonic cavity of the SERS device; permitting, using the photonic cavity, a (Continued)

fluid to flow freely into and out of the SERS device; causing, within the photonic cavity, an interaction among the incident light, the fluid, and a nanowire array of the SERS device to create scattered light; converting the scattered light into an electrical signal; and analyzing the electrical signal to determine whether a contaminant exists in the fluid.

28 Claims, 15 Drawing Sheets

(51) Int. Cl.
  *G01N 33/28* (2006.01)
  *G01N 33/18* (2006.01)
  *G01N 33/49* (2006.01)
  *G01N 21/05* (2006.01)
  *G01N 21/03* (2006.01)
(52) U.S. Cl.
  CPC ............ *G01N 21/94* (2013.01); *G01N 33/18* (2013.01); *G01N 33/2835* (2013.01); *G01N 33/49* (2013.01); *G01N 2201/063* (2013.01); *G01N 2201/06113* (2013.01)
(58) Field of Classification Search
  CPC ............... G01N 33/2835; G01N 33/49; G01N 2201/06113; G01N 2201/063
  See application file for complete search history.

(56) References Cited

U.S. PATENT DOCUMENTS

| | | | |
|---|---|---|---|
| 8,003,408 B2 | 8/2011 | Zhang et al. | |
| 8,687,187 B2 | 4/2014 | Cunningham | |
| 8,830,450 B2 | 9/2014 | Bond et al. | |
| 9,213,000 B2 | 12/2015 | Ozin et al. | |
| 9,272,126 B2 | 3/2016 | Cunningham et al. | |
| 9,632,032 B2* | 4/2017 | Landis | B82Y 30/00 |
| 9,733,125 B2 | 8/2017 | Liu et al. | |
| 10,466,167 B2 | 11/2019 | Nayak et al. | |
| 2003/0059820 A1* | 3/2003 | Vo-Dinh | C12Q 1/6837 506/3 |
| 2005/0176029 A1 | 8/2005 | Heller et al. | |
| 2005/0186565 A1 | 8/2005 | Malak | |
| 2006/0055920 A1 | 3/2006 | Wang et al. | |
| 2006/0055921 A1 | 3/2006 | Wang et al. | |
| 2006/0056463 A1 | 3/2006 | Wang et al. | |
| 2006/0147148 A1 | 7/2006 | Wang et al. | |
| 2010/0085566 A1 | 4/2010 | Cunningham | |
| 2011/0128537 A1 | 6/2011 | Bond et al. | |
| 2011/0176130 A1 | 7/2011 | Gu et al. | |
| 2012/0078523 A1 | 3/2012 | Letant et al. | |
| 2012/0276549 A1 | 11/2012 | Cunningham et al. | |
| 2012/0281209 A1 | 11/2012 | Bai | |
| 2013/0169960 A1 | 7/2013 | Cunningham | |
| 2013/0171667 A1 | 7/2013 | Unnimadhava Kurup Soudamini Amma et al. | |
| 2014/0193839 A1 | 7/2014 | Cunningham | |
| 2014/0322729 A1 | 10/2014 | Fan et al. | |
| 2015/0322286 A1 | 11/2015 | Cabrini et al. | |
| 2017/0356850 A1 | 12/2017 | Gu et al. | |
| 2018/0003706 A1 | 1/2018 | Trenholm et al. | |
| 2019/0033218 A1 | 1/2019 | Gong et al. | |
| 2020/0205667 A1 | 7/2020 | Unnimadhava Kurup Soudamini Amma et al. | |

OTHER PUBLICATIONS

Rahomaki, Jussi, et al.; "Horizontal Slot Waveguide Channel for Enhanced Raman Scattering"; Optics Express; vol. 21, Issue 7; 2013; 9 pages.

Weng, Binbin, et al. "Continuous-Wave Mid-Infrared Photonic Crystal Light Emitters at Room Temperature"; Appl. Phys. B.; vol. 123; Dec. 26, 2016; 5 pages.

Weng, Binbin, et al.; "Responsivity Enhancement of Mid-Infrared PbSe Detectors Using CaF2 Nano-Structured Antireflective Coatings"; Appl. Phys. Lett.; vol. 104; Jan. 14, 2014; 5 pages.

PCT International Search Report; Application No. PCT/US2020/020454; dated May 20, 2020; 3 pages.

PCT Written Opinion of the International Searching Authority; Application No. PCT/US2020/020454; dated May 20, 2020; 12 pages.

* cited by examiner

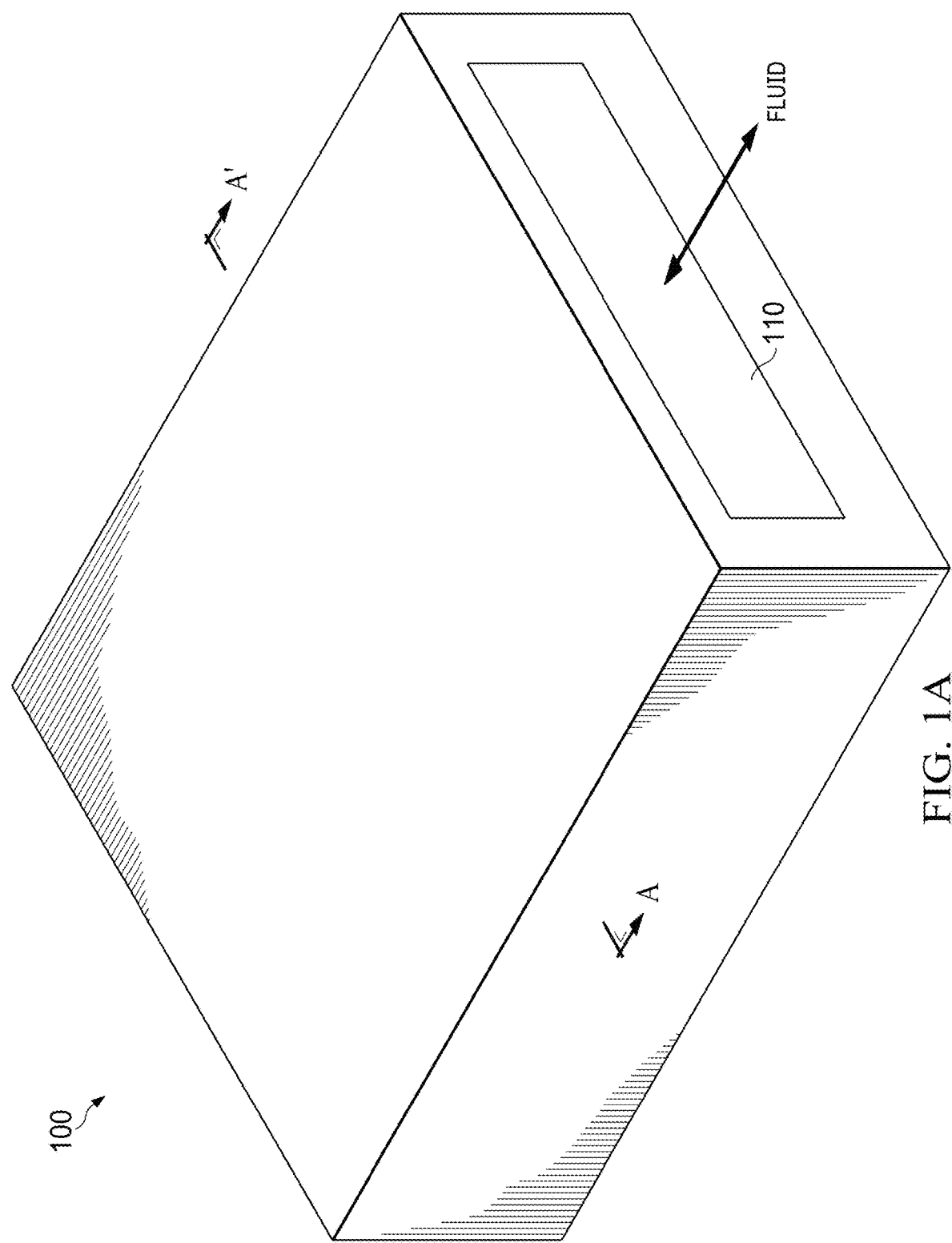

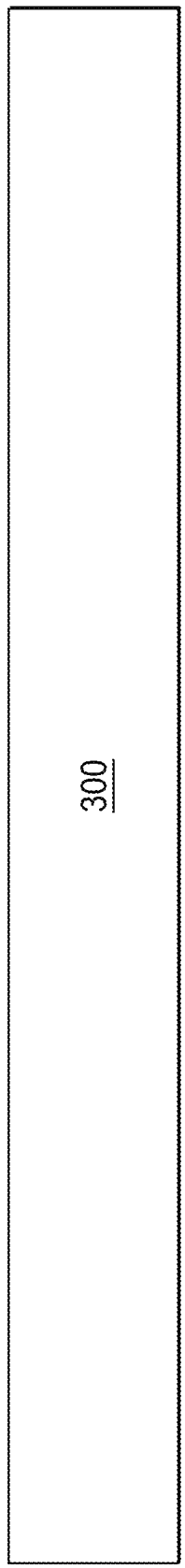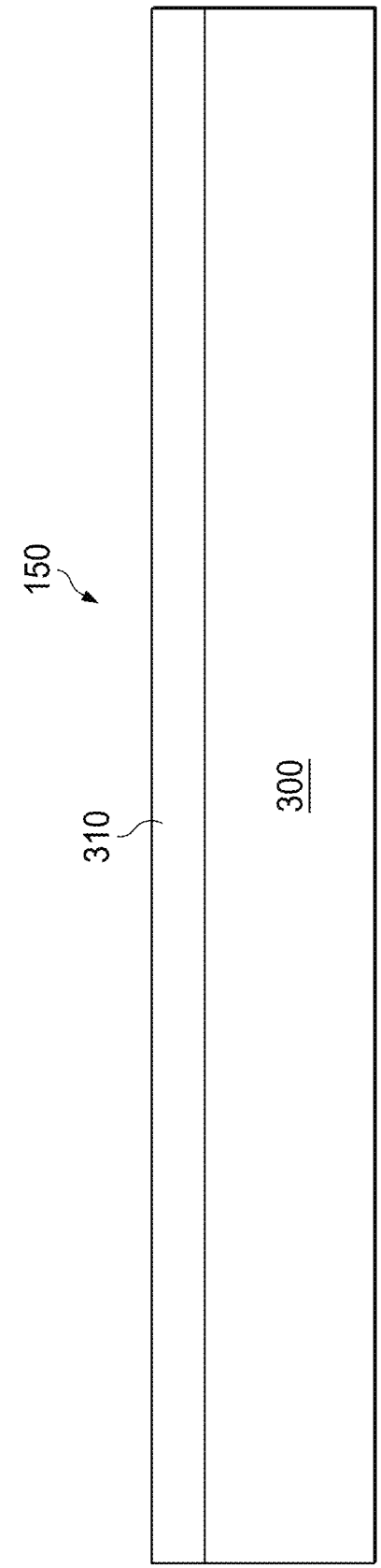

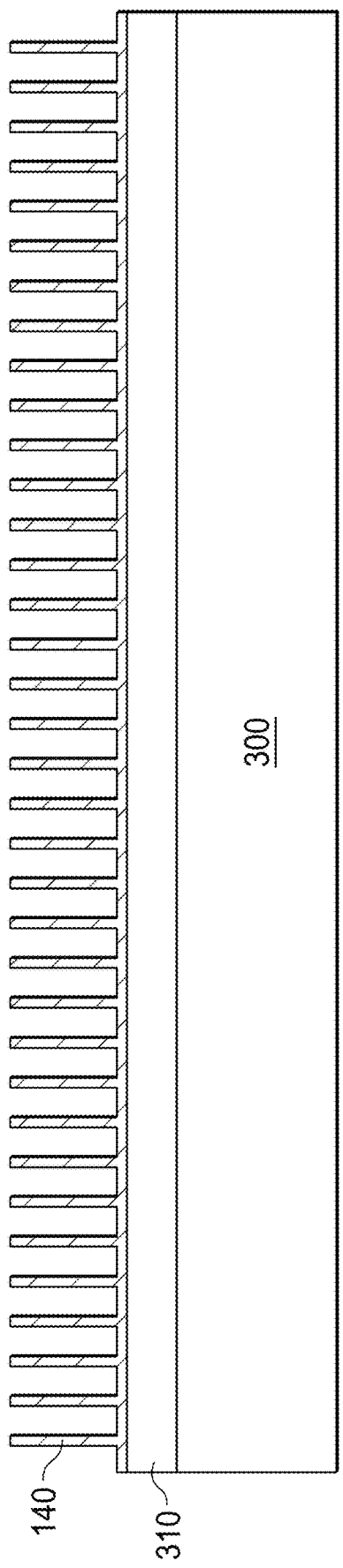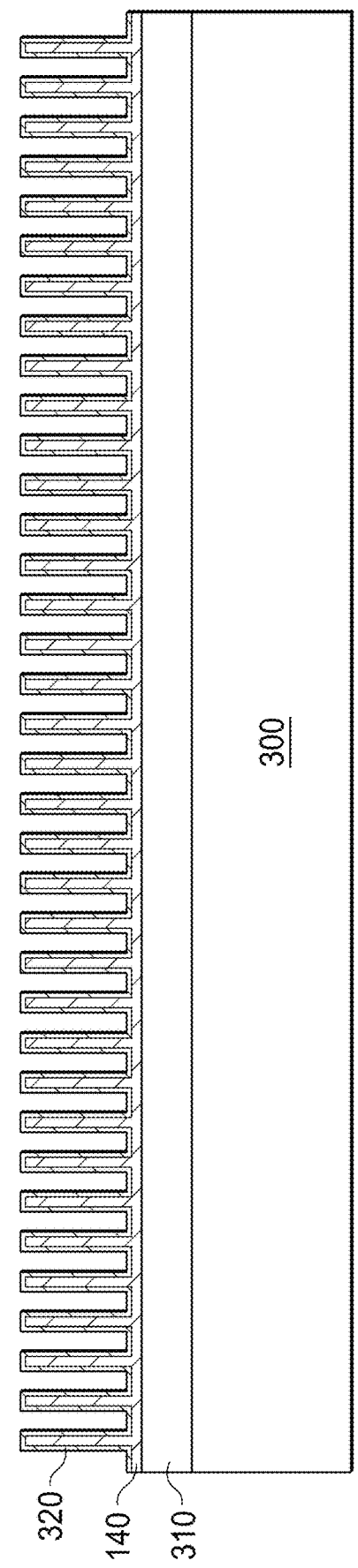

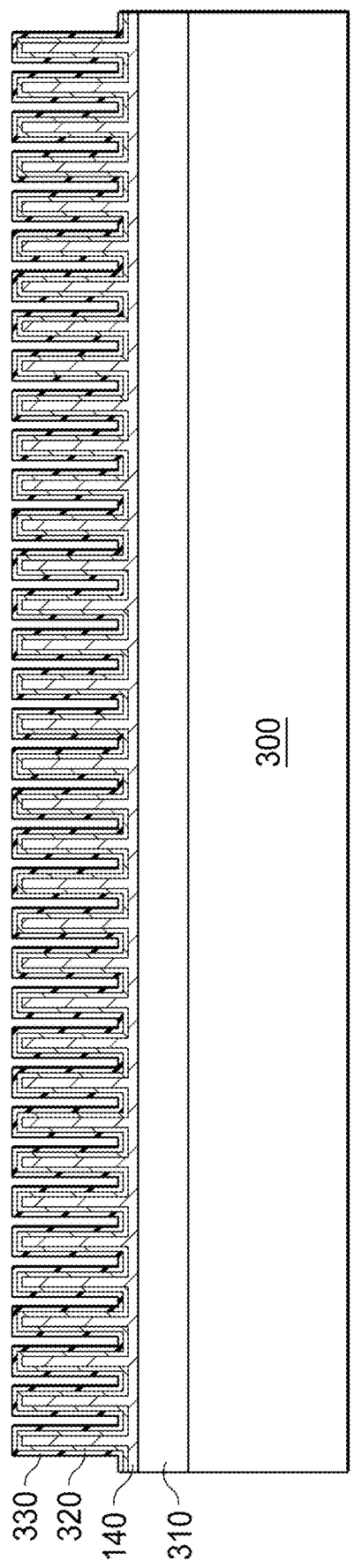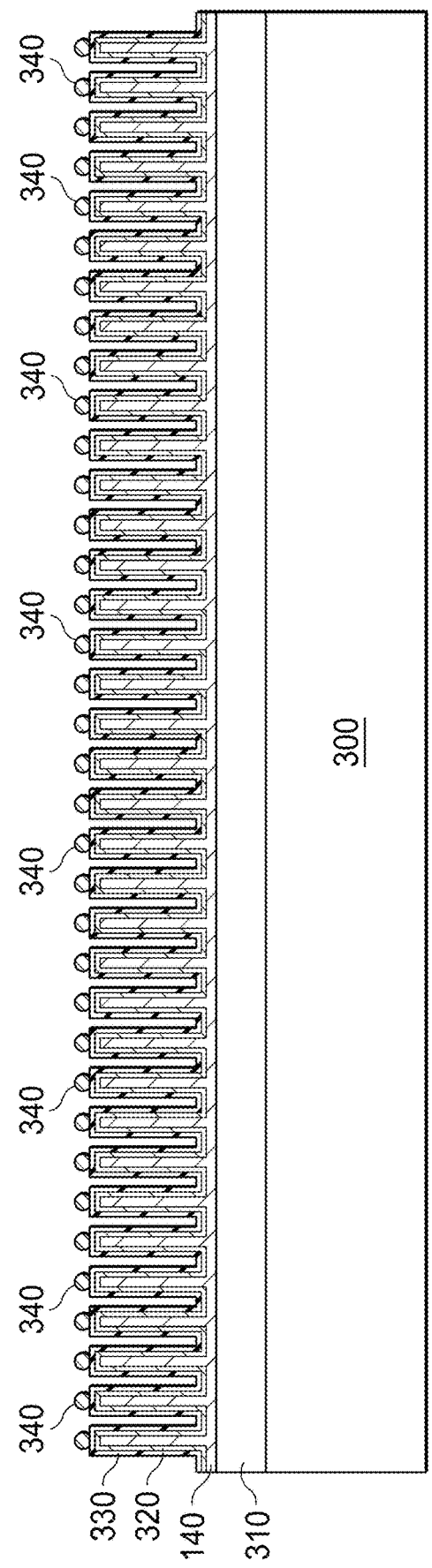

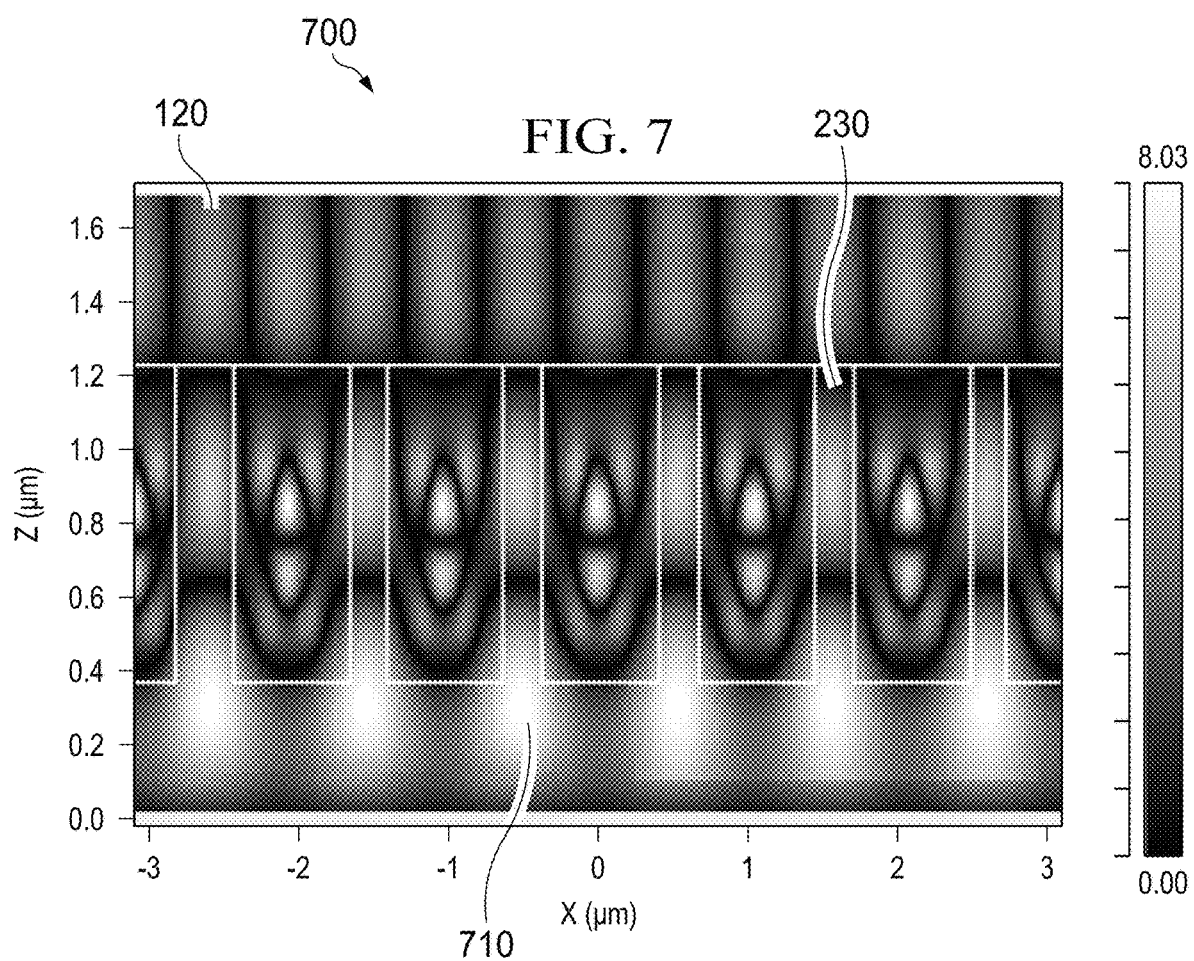

AUTOMATIC, REAL-TIME SURFACE-ENHANCED RAMAN SCATTERING (SERS) ANALYSIS

CROSS-REFERENCE TO RELATED APPLICATIONS

This is a national stage of Int'l Patent App. No. PCT/US2020/020454 filed on Feb. 28, 2020 by The Board of Regents of the University of Oklahoma and titled "Automatic, Real-Time Surface-Enhanced Raman Scattering (SERS) Analysis," which claims priority to U.S. Prov. Patent App. No. 62/812,629 filed on Mar. 1, 2019 by The Board of Regents of the University of Oklahoma and titled "Photonic Cavity Assisted Superhydrophobic Non-Structured Surface Enhanced Raman Scattering (SERS) Sensor and Methods of Use," which are incorporated by reference.

BACKGROUND

Raman scattering occurs when an incident light emits from a source and interacts with a sample material due to an energy exchange from vibration or another force, causing a small amount of scattered light to inelastically scatter. In this context, inelastically means that the scattered light has a different energy or different wavelength from the incident light. That phenomenon is called the Raman effect. Raman spectroscopy observes the scattered light to determine information about the sample material.

SERS employs nanoscale, roughened, metal surfaces to amplify the amount of inelastically-scattered light by many orders of magnitude. This makes it possible to observe small concentrations of materials, even single molecules, in the sample material. Thus, one can use SERS to detect contaminants in water, oil, blood, and other sample materials.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

FIG. 1A is a perspective schematic view of a SERS device according to an embodiment of the disclosure.

FIGS. 3A-3F illustrate a fabrication process of the wafer and nanowire array in FIG. 1B.

FIG. 7 a graph of EMF distribution in the substrate in FIGS. 1A and 1B.

DETAILED DESCRIPTION

Figure 1B:
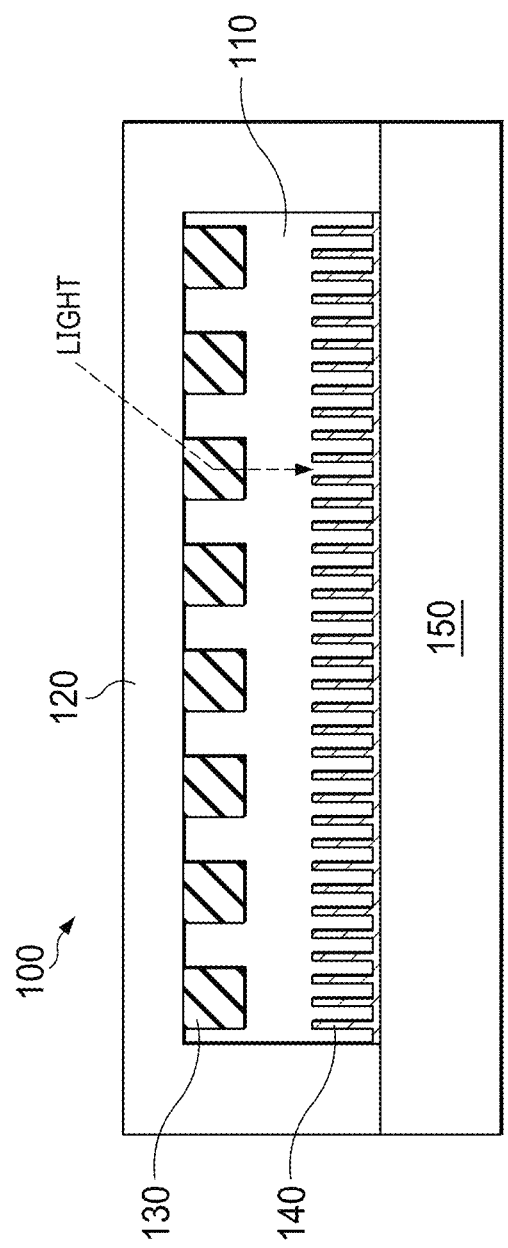
FIG. 1B is a cross-sectional schematic view of the SERS device taken along the A-A' cut line in FIG. 1A.

Current SERS analyses require a technician to obtain a sample material, for instance a fluid; obtain SERS particles, for instance loose metal particles; combine the sample material and the SERS particles into a combination; vibrate the combination; separate the SERS particles from the sample material; and analyze the SERS particles for evidence of contaminants. A fluid cannot continue to flow while the technician performs those steps. Thus, there is a need for a SERS analysis that is automatic, meaning it does not require a technician's or other person's intervention and is therefore independent of human intervention, and a SERS analysis that is in real time, meaning it does not stop a flow of fluid or another sample material process. In addition, only a small amount of scattered light scatters due to the Raman effect. That amount may be only about 0.0000001% of the incident light. Current SERS analyses are not sensitive enough to overcome that limitation. Thus, there is a need for a more sensitive SERS analysis. Furthermore, current SERS analyses do not analyze large volumes of sample materials and the SERS particles often become fouled by contaminants when the contaminants attached to the surfaces of the SERS particles. Thus, there is a need for SERS analyses that analyze large volumes of sample materials and implement SERS particles that do not become fouled by contaminants.

Disclosed herein are embodiments for an automatic, real-time SERS analysis. A SERS device comprises waveguides that direct light, which improves sensitivity of SERS detection. The SERS device also comprises nanowires that are superhydrophobic in order to provide fouling resistance. The waveguides and the nanowires are in a photonic cavity that permits a fluid to flow freely. The SERS device is automatic because the waveguides, nanowires, and photonic cavity can function independent of human intervention, and the SERS device functions in real time because the SERS analysis it performs does not stop a flow of the fluid. The fluid may be oil, water, or blood. Though fluids such as hazardous and non-hazardous fluids are discussed, the embodiments also apply to gases, plasmas, and vapors.

Before describing various embodiments of the present disclosure in more detail by way of exemplary description, examples, and results, it is to be understood as noted above that the present disclosure is not limited in application to the details of methods and apparatus as set forth in the following description. The present disclosure is capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

As utilized in accordance with the methods and apparatus of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges (e.g., in units of length such as micrometers or millimeters) include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example. For example, a reference to a range of 3 mm and 20 mm in diameter, or a range of 50 μm to 300 μm in thickness, is intended to explicitly include all units of measurement in the range.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" and "approximately" are used to indicate that a value includes the inherent variation of error. Further, in this detailed description, each numerical value (e.g., temperature or time) should be read once as modified by the term "about" (unless already expressly so modified), and then read again as not so modified unless otherwise indicated in context. As noted above, any range listed or described herein is intended to include, implicitly or explicitly, any number within the range, particularly all integers, including the end points, and is to be considered as having been so stated. For example, "a range from 1 to 10" is to be read as indicating each possible number, particularly integers, along the continuum between about 1 and about 10. Thus, even if specific data points within the range, or even no data points within the range, are explicitly identified or specifically referred to, it is to be understood that any data points within the range are to be considered to have been specified, and that the inventors possessed knowledge of the entire range and the points within the range. Unless otherwise stated, the terms "about" or "approximately", where used herein when referring to a measurable value such as an amount, length, thickness, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art.

As used herein, the term "substantially" means that the subsequently described parameter, event, or circumstance completely occurs or that the subsequently described parameter, event, or circumstance occurs to a great extent or degree. For example, the term "substantially" means that the subsequently described parameter, event, or circumstance occurs at least 90% of the time, or at least 91%, or at least 92%, or at least 93%, or at least 94%, or at least 95%, or at least 96%, or at least 97%, or at least 98%, or at least 99%, of the time, or means that the dimension or measurement is within at least 90%, or at least 91%, or at least 92%, or at least 93%, or at least 94%, or at least 95%, or at least 96%, or at least 97%, or at least 98%, or at least 99%, of the referenced dimension or measurement (e.g., length).

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

It should be understood at the outset that, although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

The following abbreviations apply:
Ag: silver
ASIC: application-specific integrated circuit
Au: gold
BETX: benzene, ethylbenzene, toluene, xylene
CO: carbon monoxide
$CO_2$: carbon dioxide
CPU: central processing unit
CVD: chemical vapor deposition
DSP: digital signal processor
E-beam: electron beam
EMF: electromagnetic field
EO: electrical-to-optical
FPGA: field-programmable gate array
bisulfide
$H_2S$: hydrogen sulfide
ITO: indium tin oxide
$NH_4$: ammonium
$NO_2$: nitrogen dioxide
OE: optical-to-electrical
PCW: photonic crystal waveguide
PECVD: plasma-enhanced chemical vapor deposition
pH: potential hydrogen
ppb: part(s) per billion
PVD: physical vapor deposition
RAM: random-access memory
RF: radio frequency
ROM: read-only memory
RX: receiver unit
SERS: surface-enhanced Raman scattering
Si: silicon
$SiO_2$: silicon dioxide
$S^{2-}$: sulfide
$SO^2$: sulfur dioxide
$SO_4^{2-}$: sulfate
$S_2O_3^{2-}$: thiosulfate ion
sol: solution
SRAM: static RAM
TCAM: ternary content-addressable memory
$TiO_2$: titanium dioxide
TX: transmitter unit
ZnO: zinc oxide
micrometer(s)
1D: one-dimensional
2D: two-dimensional.

FIG. 1A is a perspective schematic view of a SERS device 100 according to an embodiment of the disclosure. The SERS device 100 may also be referred to as a SERS-PCW device, detector, or sensor. The SERS device 100 comprises a photonic cavity 110 that extends across a length of the SERS device 100. The photonic cavity 110 permits a fluid to flow freely into and out of the SERS device 100 as shown. Thus, the SERS device 100 may be placed in a tube, a pipeline, a storage tank, a lagoon, a well, a downhole probe, or another medium that contains the fluid.

FIG. 1B is a cross-sectional schematic view of the SERS device 100 taken along the A-A' cut line in FIG. 1A. FIG. 1B shows the photonic cavity 110. In addition, FIG. 1B also shows that the SERS device 100 comprises a substrate 120 and a wafer 150. The substrate 120 and the wafer 150 are bonded to each other via flip-chip bonding or another suitable method to define the photonic cavity 110.

The substrate 120 comprises a waveguide layer 130. The substrate 120, including the waveguide layer 130, may comprise a dielectric material such as ITO, $SiO_2$, or $TiO_2$. The waveguide layer 130 comprises waveguides that direct light down and vertically towards the photonic cavity 110 as shown. The waveguides are arranged in a 1D grid or a 2D grid.

The wafer 150 comprises Si, oxidized Si, glass, quartz, or another suitable material. The wafer 150 comprises a nanowire array 140 affixed to a top side of the wafer 150. The nanowire array 140 comprises nanowires that are vertically aligned with each other and are arranged in a 2D grid. The nanowires serve as SERS particles, or nanoparticles. The nanowires may comprise a metal composition such as Ag, Au, Si, $TiO_2$, or ZnO; a colloidal shape; a metal coating such as a gold coating; and a spun-coated top. The metal composition has a plasmon resonance frequency that aids in SERS. The colloidal shape generates strong plasmon, which makes the SERS analysis more sensitive. The gold coating is superhydrophobic to provide fouling resistance and thus prevent build-up of contaminants and allow a continual flow of the fluid. The spun-coated top creates SERS hot spots, which are areas of highly-local SERS as described below with respect to FIG. 7.

Figure 2A:
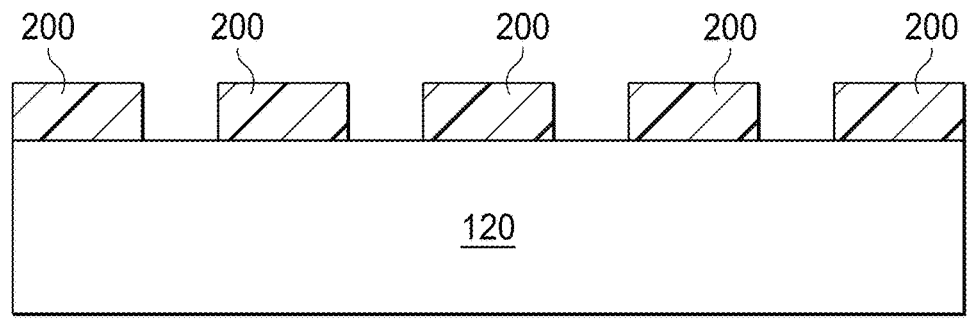
FIGS. 2A-2D illustrate a fabrication process of the substrate and waveguide layer in FIG. 1B.
Figure 2B:
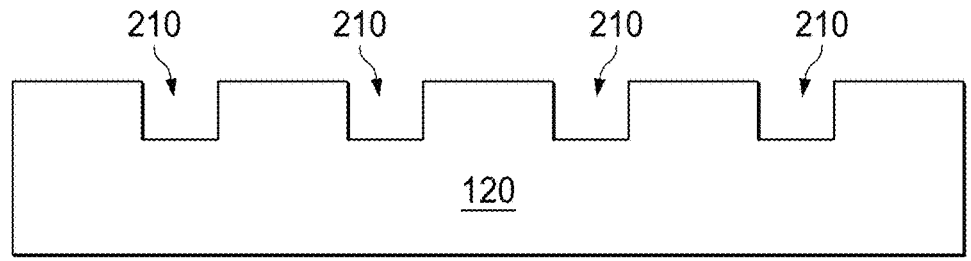
Figure 2C:
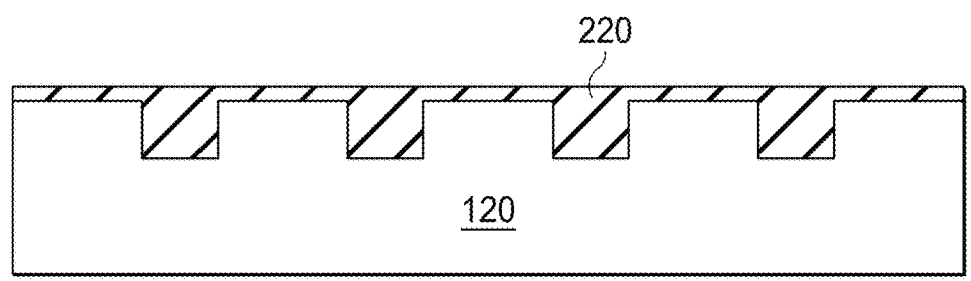
Figure 2D:
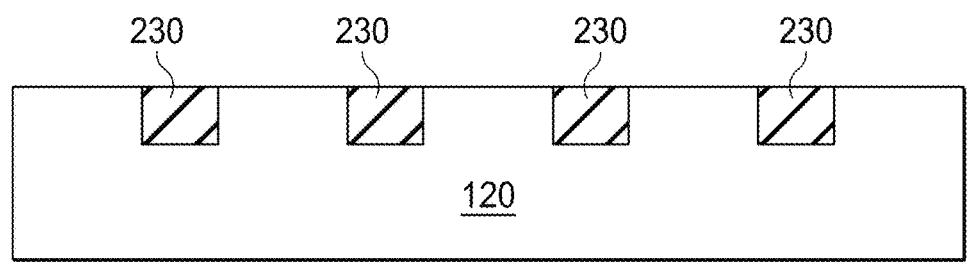

FIGS. 2A-2D illustrate a fabrication process of the substrate 120 and waveguide layer 130 in FIG. 1B. In FIGS. 2A-2D, the orientation of the substrate 120 is flipped compared to FIGS. 1A and 1B so that the top of the substrate 120 in FIGS. 1A and 1B is at the bottom of the page in FIGS. 2A-2D. FIG. 2A shows the substrate 120 with a photoresist 200 on top. A fabricator may use E-beam lithography patterning to grow the photoresist 200. FIG. 2B shows the substrate 120 with the photoresist 200 and portions 210 removed. The fabricator may remove the portions 210 using dry etching, then remove the photoresist 200 by soaking the substrate 120 in a photoresist thinner solution. FIG. 2C shows the substrate 120 with an Si layer 220 on top. Instead of Si, the Si layer 220 may be air, ITO, or $TiO_2$. The fabricator may use a PECVD process to grow the Si layer 220. Finally, FIG. 2D shows the substrate 120 with waveguides 230. The fabricator may perform chemical-mechanical polishing of the Si layer 220 to remove overgrown portions of the Si layer 220 and leave the waveguides 230. The waveguides 230 make up the waveguide layer 130 in FIGS. 1A and 1B. FIG. 1B shows a left portion and a right portion of the substrate 120 extending down in order to provide a connection to the wafer 150. In FIG. 2D, though not shown, the left portion and the right portion of the substrate would extend up.

FIGS. 3A-3F illustrate a fabrication process of the wafer 150 and nanowire array in FIG. 1B. FIG. 3A shows a substrate 300. The substrate 300 comprises glass, quartz, Si, $SiO_2$-coated Si, or another suitable material. FIG. 3B shows the substrate 300 with a seeding layer 310 on top. A fabricator may use a sputtering or sol-gel method to deposit the seeding layer 310 on top of the substrate 300. The seeding layer 310 may be a semiconductor material such as Ag, Au, Si, or ZnO. Together, the substrate 300 and the seeding layer 310 form the wafer 150. FIG. 3C shows the nanowire array 140 on top of the seeding layer 310. The fabricator may grow the nanowire array 140 on top of the seeding layer 310 using a CVD, an electrochemical etching, a hydrothermal, or another suitable method. FIG. 3D shows a gold layer 320 on top of the nanowire array 140. The fabricator may use a PVD method such as sputtering, thermal evaporation, or E-beam evaporation to apply the gold layer 320 as a coating. The gold layer 320 provides hydrophobicity. FIG. 3E shows a damping suppression layer 330 on top of the gold layer 320. The fabricator may use a sputtering or atomic layer deposition method to apply the damping suppression layer 330. The damping suppression layer 330 may comprise a Parylene monomer, $SiO_2$, or $TiO_2$. FIG. 3F shows nanoparticles 340 on top of the damping suppression layer 330. The fabricator may use a pipe spraying or layered ionic deposition method to apply the nanoparticles 340.

Figure 4:
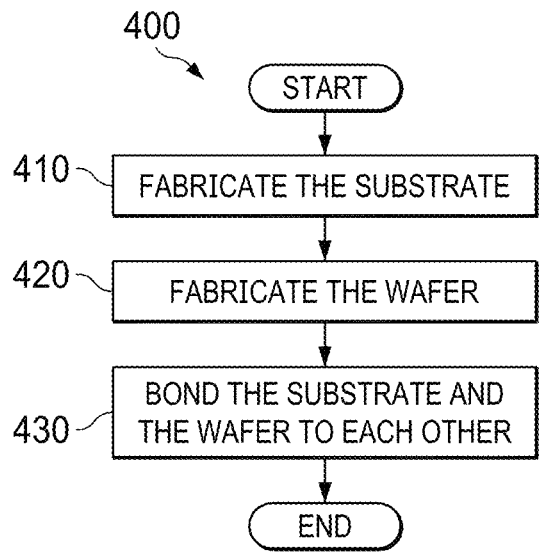
FIG. 4 is a flowchart illustrating a method of fabricating the SERS device in FIGS. 1A and 1B.

FIG. 4 is a flowchart illustrating a method 400 of fabricating the SERS device 100 in FIGS. 1A and 1B. At step 410, the substrate 120 is fabricated. For instance, a fabricator fabricates the substrate 120 as shown in FIGS. 2A-2D. At step 420, the wafer 150 is fabricated. For instance, the fabricator fabricates the wafer 150 as shown in FIGS. 3A-3F. Finally, at step 430, the substrate 120 and the wafer 150 are bonded to each other. For instance, the fabricator bonds the substrate 120 and the wafer 150 to each other using flip-chip bonding.

Figure 5:
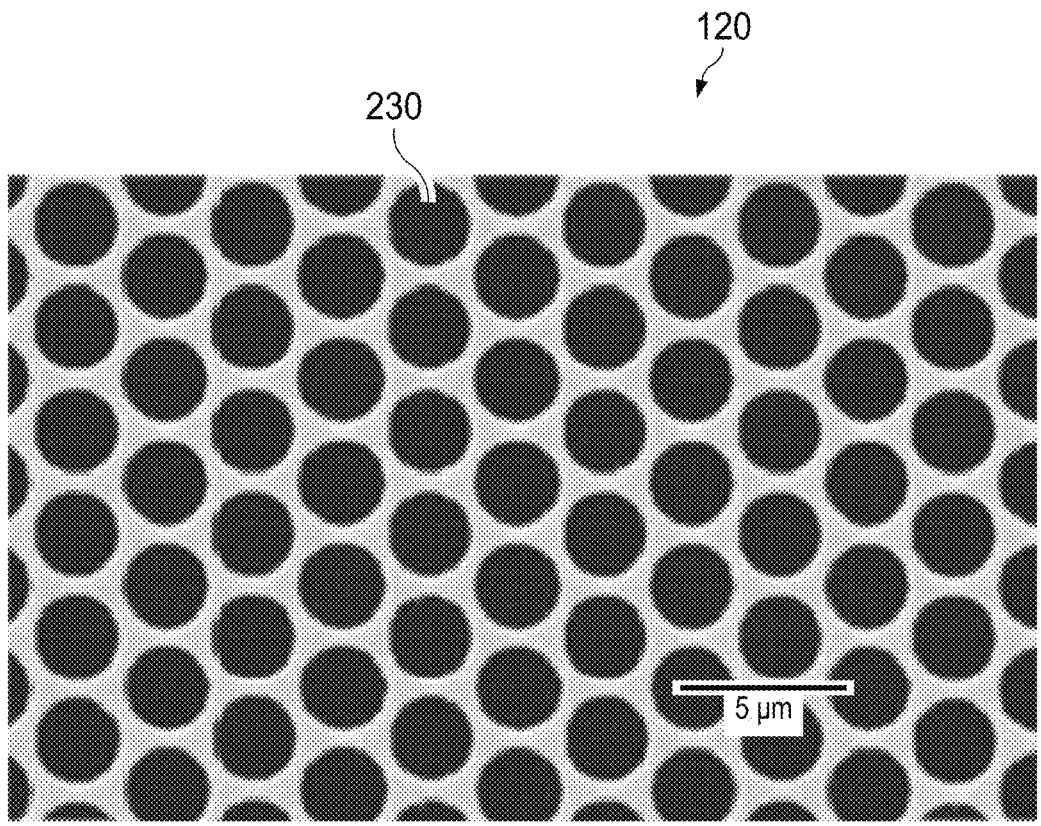
FIG. 5 is a top photographic view of the substrate in FIGS. 1A and 1B.

FIG. 5 is a top photographic view of the substrate 120 in FIGS. 1A and 1B. As shown, the substrate 120 comprises the waveguides 230 in FIG. 2D. The waveguides 230 are arranged in a 2D grid. The tops of the waveguides 230 are circular, so the waveguides 230 extend cylindrically down towards the photonic cavity 110. Centers of the waveguides 130 are spaced about 5 µm apart as shown.

Figure 6A:
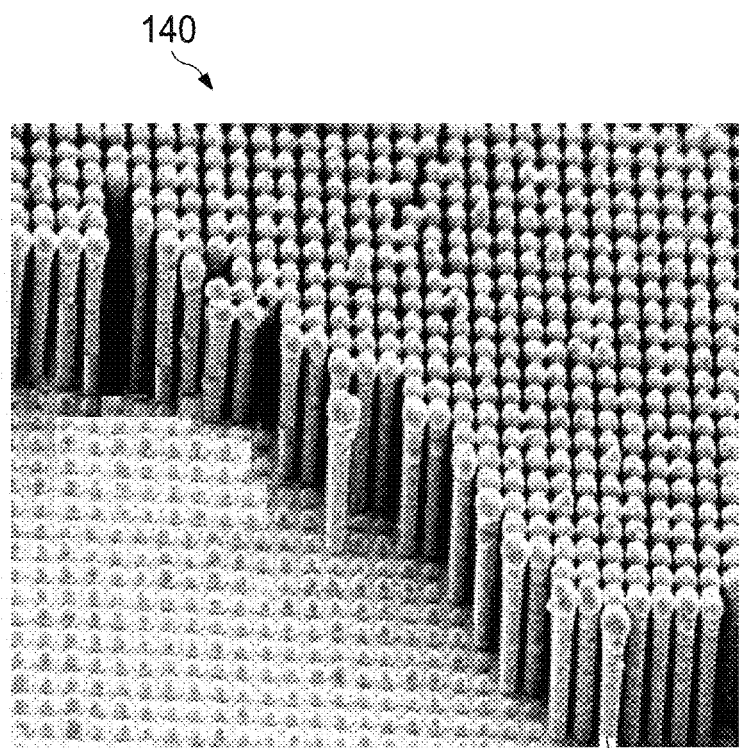
FIG. 6A is a perspective photographic view of the nanowire array in FIGS. 1A and 1B.
Figure 6B:
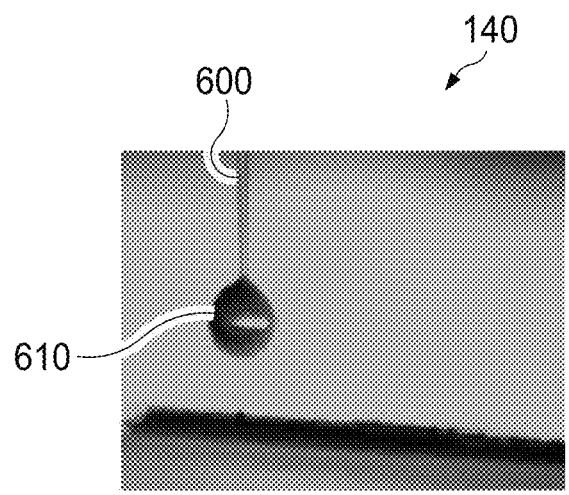
FIG. 6B is a side photographic view of a nanowire in FIG. 6A.

FIG. 6A is a perspective photographic view of the nanowire array 140 in FIGS. 1A and 1B. The nanowire array 140 comprises nanowires 600 arranged in a 2D grid, which may be referred to as a "forest." FIG. 6B is a side photographic view of a nanowire 600 in FIG. 6A. The nanowire 600 is resisting a droplet 610 of water as shown due to the superhydrophobic gold coating of the nanowire 600.

FIG. 7 is a graph 700 of EMF distribution in the substrate 120 in FIGS. 1A and 1B. An x-axis represents a width of the substrate 120 in µm, and a y-axis represents a height of the substrate in µm. An energy intensity scale indicates energy intensity from a lowest value of 0 in black to a highest value of 8.03 in white. The values are arbitrary and relative to each other. The graph 700 shows the substrate 120 in FIGS. 1A and 1B and the waveguides 230 in FIG. 2D, as well as hot spots 710. The hot spots 710 are described above with respect to FIG. 1B. The hot spots 710 are white or near-white and thus correspond to the most intense areas of the graph 700.

Figure 8:
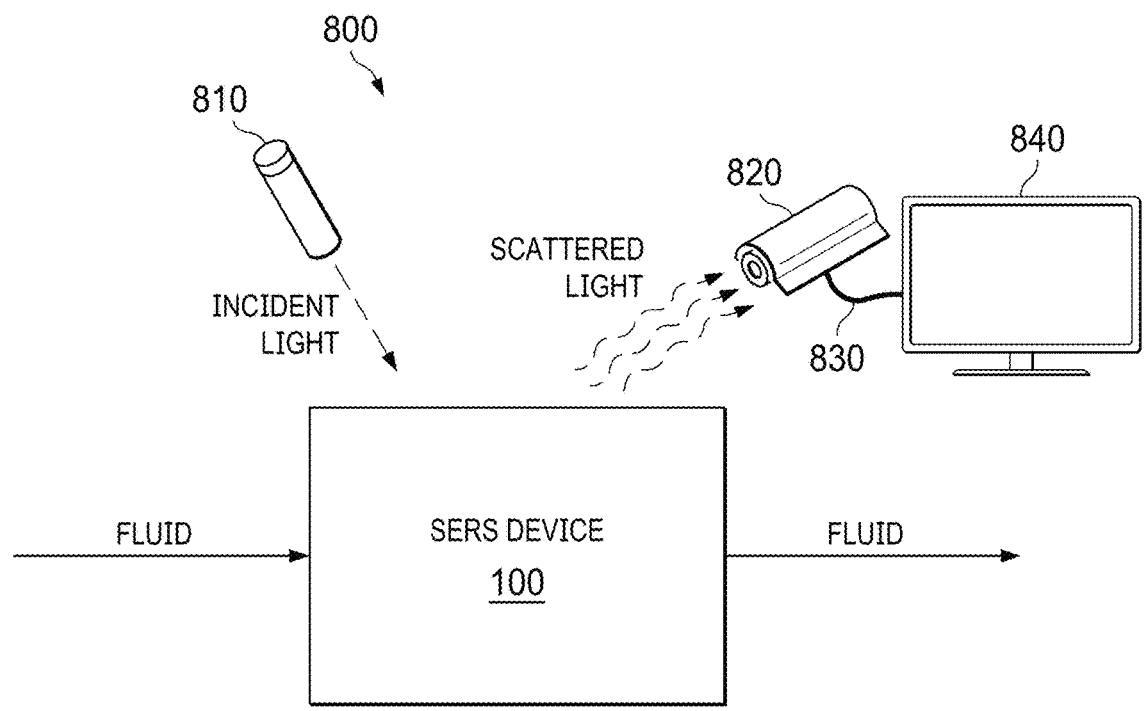
FIG. 8 is a schematic diagram of a SERS detection system according to an embodiment of the disclosure.

FIG. 8 is a schematic diagram of a SERS detection system 800 according to an embodiment of the disclosure. The SERS detection system 800 comprises a light source 810, the SERS device 100, a photodetector 820, an electrical medium 830, and a computer 840. The light source 810 may be a laser. The electrical medium 830 may be a cable or cord. The computer 840 may be a group of networked computers.

In operation, the light source 810 emits an incident light towards the SERS device 100. Within the SERS device 100, the incident light enters the waveguide layer 130, travels through the waveguides 230 and vertically towards the photonic cavity 110, and causes the fluid to interact with the nanowire array 140. As a result of that interaction, scattered light scatters from the SERS device 100 due to the Raman effect and enters the photodetector 820. The photodetector 820 receives the scattered light, converts the scattered light into an electrical signal, and transmits the electrical signal to the computer 840 via the electrical medium 830. The computer 840 analyzes the electrical signal to determine whether a contaminant exists in the fluid and, if so, the concentration of the contaminant. The computer 840 may comprise modeling and prediction software to determine spatial and temporal changes in the fluid, which may prompt treatment of the fluid.

Figure 9:
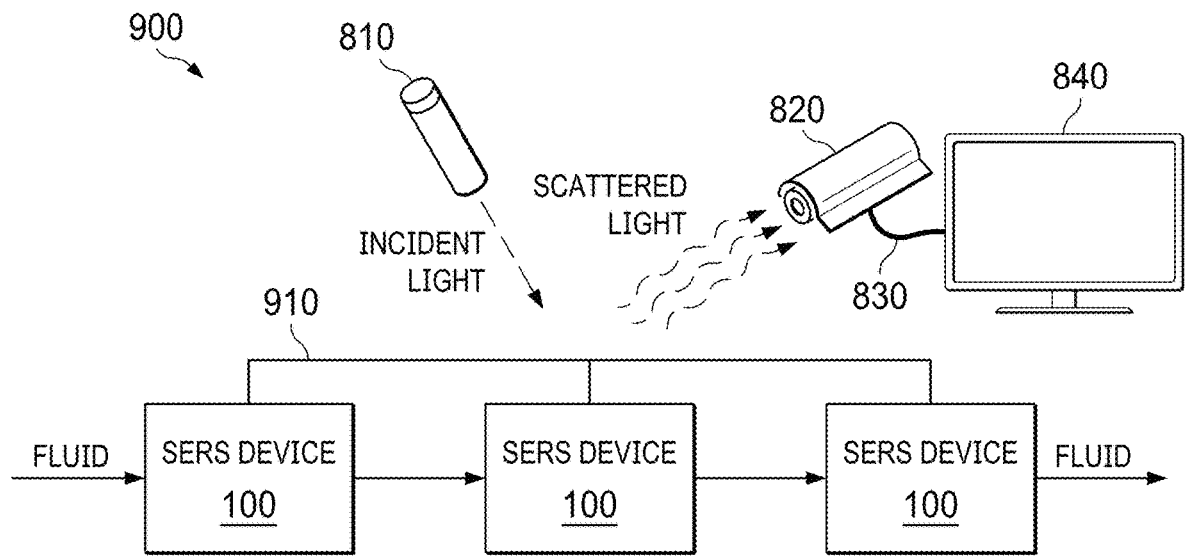
FIG. 9 is a schematic diagram of a SERS detection system according to another embodiment of the disclosure.

FIG. 9 is a schematic diagram of a SERS detection system 900 according to another embodiment of the disclosure. The SERS detection system 900 is similar to the SERS detection system 800 in FIG. 8. Specifically, the SERS detection system 800 comprises the light source 810, the photodetector 820, the electrical medium 830, and the computer 840. However, unlike the SERS detection system 800, which comprises one SERS device 100, the SERS detection system 900 comprises three SERS devices 100. In addition, the SERS detection system 900 comprises three optical fibers 910 coupling the light source 810 and the photodetector 820 to the SERS devices 100 in order to communicate the incident light and the scattered light. Thus, the SERS detection system 900 may analyze the fluid in multiple locations.

Figure 10:
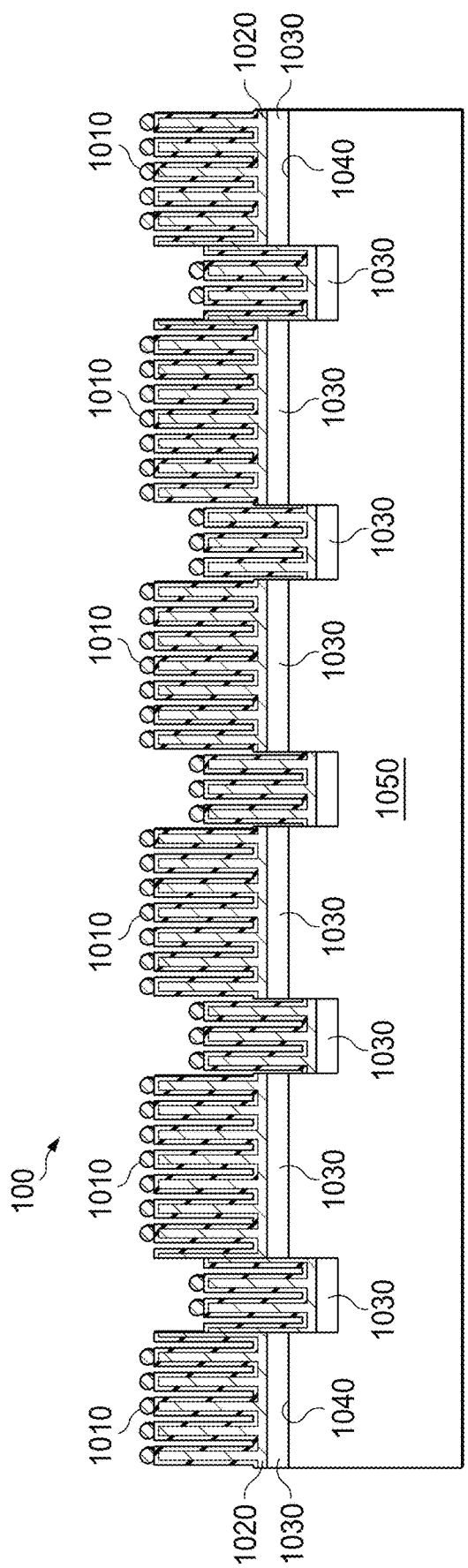
FIG. 10 is another cross-sectional schematic view of the SERS device taken along the A-A' cut line in FIG. 1A.

FIG. 10 is another cross-sectional schematic view of a SERS device 100 taken along the A-A' cut line in FIG. 1A. FIG. 10 shows that the SERS device 100 comprises nanoparticles 1010, nanowires 1020, a seeding layer 1030, waveguides 1040, and a substrate 1050. The nanoparticles 1010 are similar to the nanoparticles 340. The nanowires 1020 form a nanowire array similar to the nanowire array 140. The seeding layer 1030 is similar to the seeding layer 310. The waveguides 1040 form a waveguide array similar to the waveguide array 130. The substrate 1050 is similar to the substrate 300. Unlike in FIG. 1B, which shows the waveguide array 130 opposing the nanowire array 140 on different sides of the SERS device 100, FIG. 10 shows the waveguides 1040 and the nanowires complementing each other on the same side of the SERS device 100.

Figure 11A:
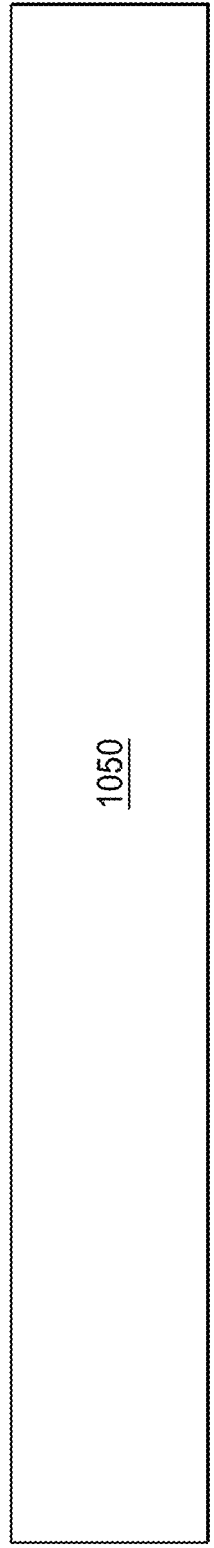
FIGS. 11A-11H illustrate a fabrication process of the SERS device in FIG. 10.
Figure 11B:
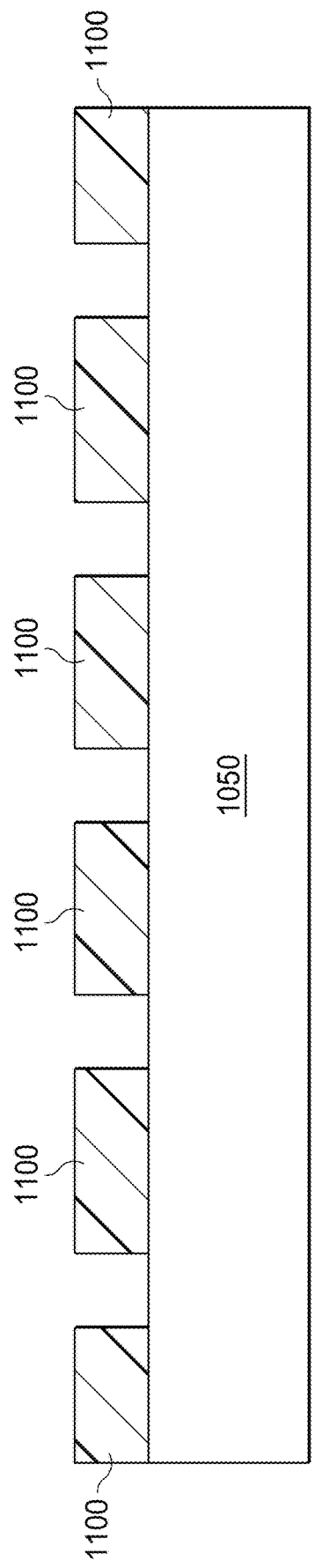
Figure 11C:
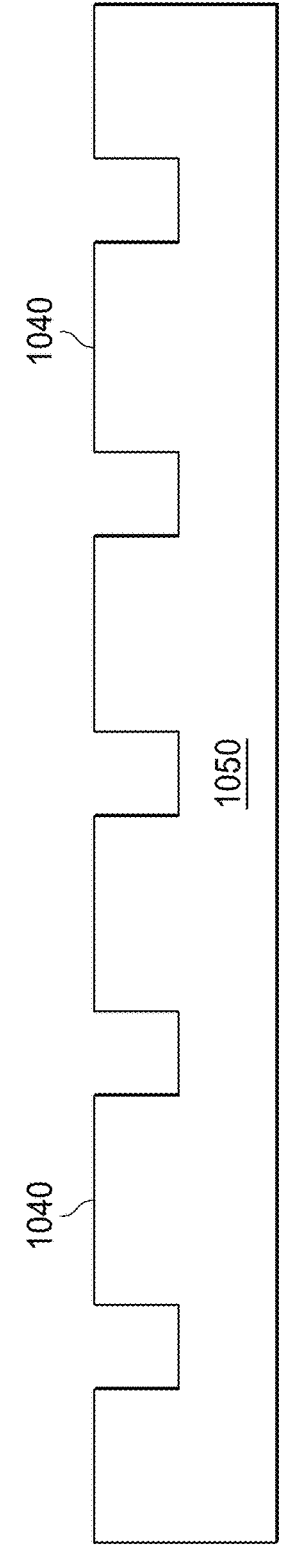
Figure 11D:
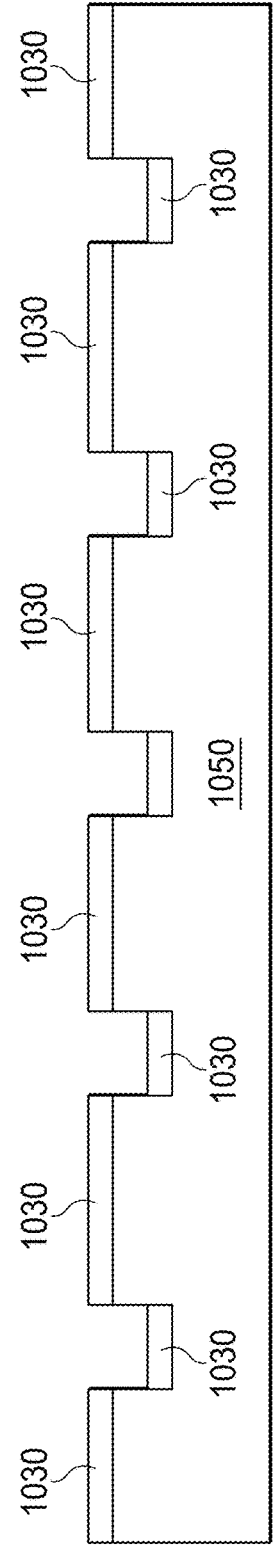
Figure 11E:
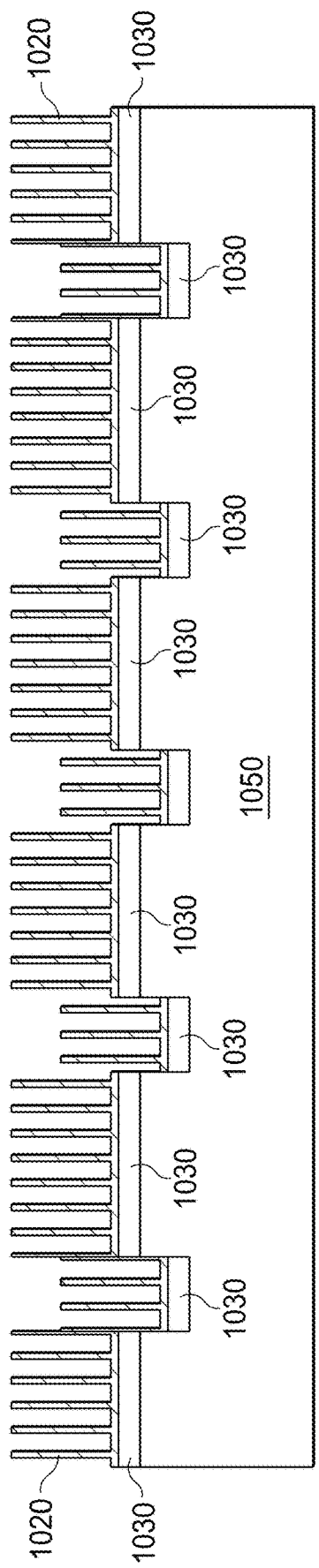
Figure 11F:
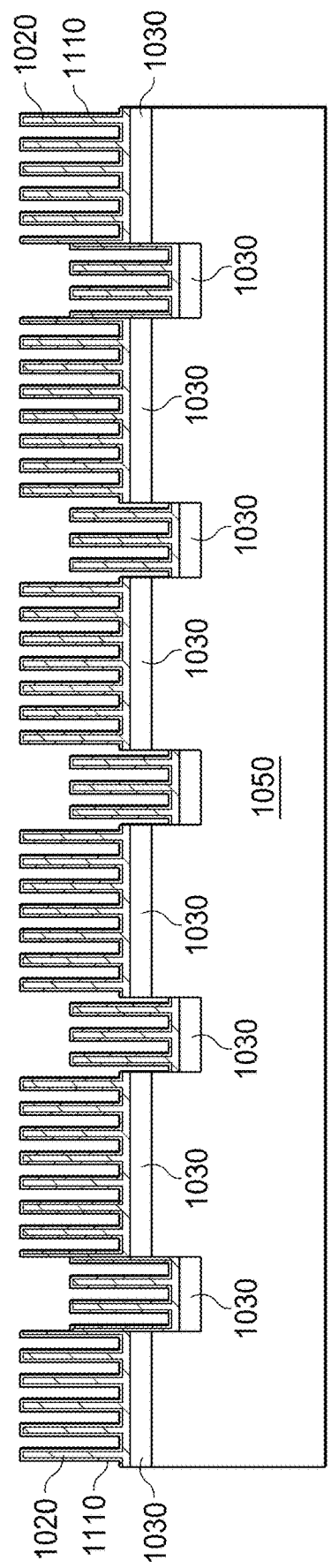
Figure 11G:
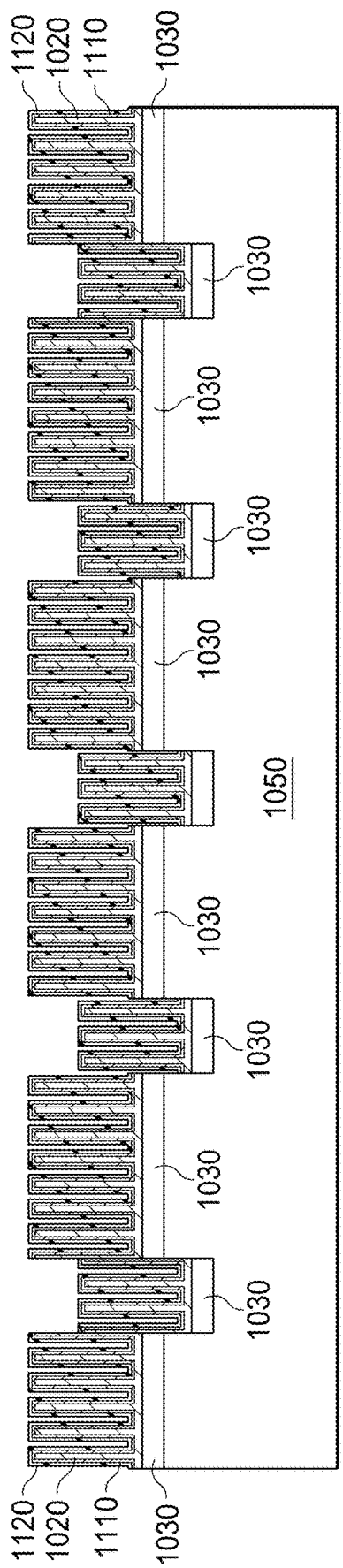
Figure 11H:
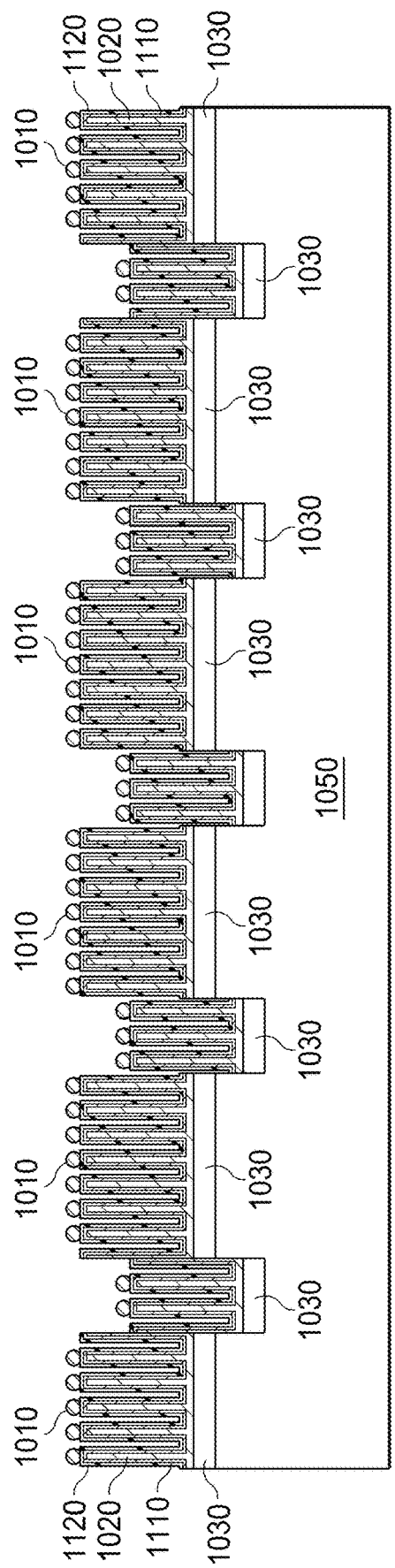

FIGS. 11A-11H illustrate a fabrication process of the SERS device 100 in FIG. 10. FIG. 11A shows a substrate 1050 similar to the substrate in FIG. 3A. FIG. 11B shows a photoresist 1100 patterned on top of the substrate 1050 similar to FIG. 2A. FIG. 11C shows the waveguides 1040 etched into the substrate 1050 similar to FIGS. 2B-2D. FIG. 11D shows the seeding layer 1030 deposited on top of the substrate 1050 similar to FIG. 3B. FIG. 11E shows the nanowires 1020 grown on top of the seeding layer 1030 similar to FIG. 3C. FIG. 11F shows a gold layer 1110 applied on top of the nanowires 1020 similar to FIG. 3D. FIG. 11G shows a damping suppression layer 1120 applied on top of the gold layer 1110 similar to FIG. 11H. FIG. 11H shows nanoparticles 1010 applied on top of the damping suppression layer 1120 similar to FIG. 3F.

Figure 12:
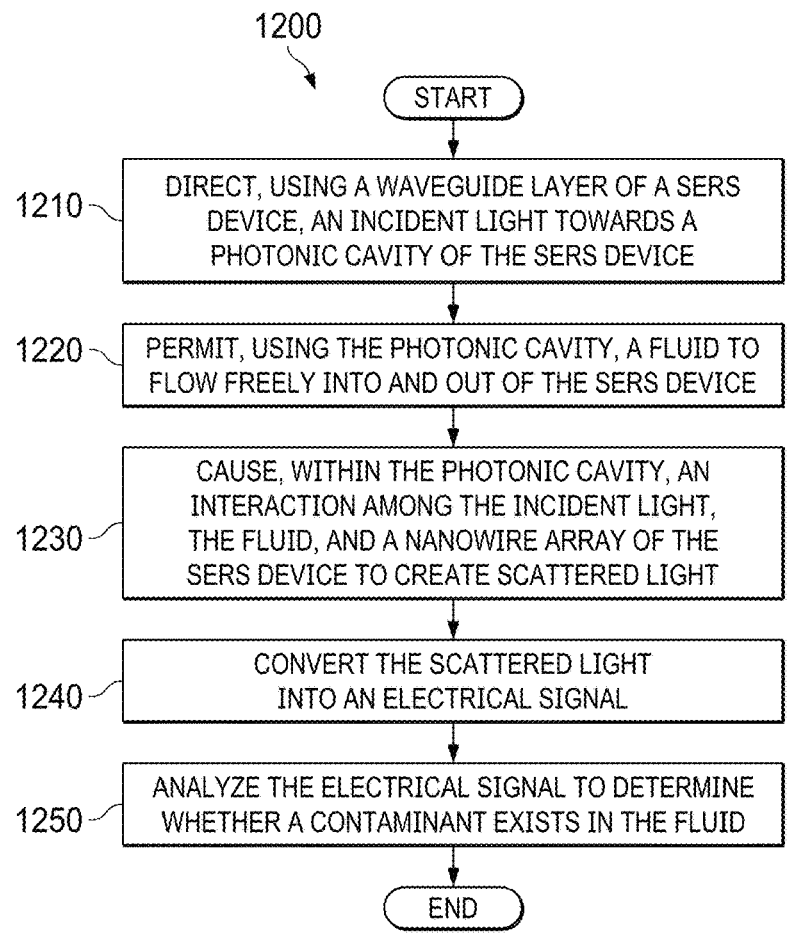
FIG. 12 is a flowchart illustrating a method of performing a SERS analysis according to an embodiment of the disclosure.

FIG. 12 is a flowchart illustrating a method 1200 of performing a SERS analysis according to an embodiment of the disclosure. At step 1210, using a waveguide layer of a SERS device, an incident light is directed towards a photonic cavity of the SERS device. For instance, the waveguide layer 130 directs the incident light towards the photonic cavity 110. At step 1220, using the photonic cavity, a fluid is permitted to flow freely into and out of the SERS device. The fluid may be oil, water, or blood. At step 1230, within the photonic cavity, an interaction among the incident light, the fluid, and a nanowire array of the SERS device is caused to create scattered light. For instance, the nanowire array is the nanowire array 140. The scattered light may be inelastically scattered via the Raman effect. At step 1240, the scattered light is converted into an electrical signal. For instance, the photodetector 820 converts the scattered light.

Finally, at step 1250, the electrical signal is analyzed to determine whether a contaminant exists in the fluid. For instance, the computer 840 analyzes the electrical signal. The computer 840 may further analyze the electrical signal to determine a concentration of the contaminant.

The SERS device 100 has numerous applications. In a first embodiment, the SERS device 100 detects dissolved organic and inorganic compounds in produced waters. The SERS device 100 analyzes dissolved organic compounds present in water from regulated BETX to chemical additives used to facilitate fracking or as biocides; polyoxy-anions and metals including regulated bromate, chlorite, nitrate, and nitrite, as well as unregulated borate and phosphate; dissolved metal ions that form polyoxy-anions such as aluminum, antimony, arsenic, chromium, and selenium. The SERS device 100 analyzes oil, gas, and other sample materials over a range of salinity and pH. The SERS device 100 does so in environments such as oilfield production waters, pipelines, storage tanks, well pads, gas plants, and refineries. The SERS analysis may prompt treatment such as introducing a chemical additive, changing a biocide concentration, reuse of the fluid, or release of the fluid into receiving waters. An analysis of flowback water composition provides information regarding geochemical changes in a subsurface during fracking treatments. The SERS device 100 may be deployed in the subsurface between fracking activity and sensitive aquifers to protect those aquifers by determining the degradation, adsorption, or transportation of fracking chemicals.

In a second embodiment, the SERS device 100 analyzes sulfur species in the aqueous phase. The sulfur species include $H_2S$, $HS^-$, $S^{2-}$, $SO^2$, $SO_4^{2-}$, and $S_2O_3^{2-}$. The conversion of water-soluble sulfur oxyanions to a variety of reduced sulfur species is differentially associated with the corrosion of carbon-steel corrosion, for instance in oilfield production waters, pipelines, storage tanks, well pads, gas plants, and refineries. The SERS device 100 is a highly sensitive and selective in-situ detector that allows real-time analyses to monitor the impact of corrosion control measures. The SERS device 100 may be coupled with simulation modeling and prediction software to provide real-time analyses of the rates of sulfur transformation and thereby help assess the degree of corrosion risk to the metallic infrastructure. The sensors may be used for hazardous emission detection, corrosion control, and process monitoring.

Traditional approaches for limiting corrosion and maintaining the integrity of the metallic infrastructure in the water, oil, and gas industry have not been successful enough. In most cases, corrosion is differentially associated with the conversion of various sulfur oxyanions to a variety of more corrosive, reduced, sulfur end products. The measurement of these processes has proven challenging throughout the water, oil, and gas infrastructure. Monitoring the impact of corrosion control measures has also been less than satisfactory. Typically, approaches to corrosion control involve the use of biocides, corrosion inhibitors, or combinations of such approaches. Monitoring efficacy of the approach is often left to third-party operators with variable results.

The SERS device 100 may be placed in-situ to provide real-time data on the kinetics of depletion of various sulfur oxyanions as well as the production of reduced sulfur products. The SERS device 100 may monitor sulfur oxyanions in the aqueous phase as these compounds readily partition to this phase and may be compatible with oily environments.

In a third embodiment, the SERS device 100 is an online dissolved oxygen sensor for challenging environments. The measurement of oxygen is necessary for many industries and particularly for the oil and gas sector. For example, the presence of oxygen in seawater used for water-flooding of petroleum reservoirs can have an adverse effect on reservoir injectivity and on the long-term integrity of the carbon-steel material used to process the injection water. Dissolved oxygen is very corrosive. A common technology for removing oxygen from the seawater is by means of a vacuum de-aeration system followed by treatment with oxygen scavengers. Similarly, the presence of oxygen and water in natural gas pipelines can result in corrosion and may lead to catastrophic leaks. Though specifications vary from pipeline to pipeline, newer specifications have trended downwards in recent years. Dissolved oxygen requirements are often strict and must be reduced to <40 ppb. When these limits are exceeded, the installation of oxygen removal efforts is needed.

There are four basic methods for the determination of dissolved oxygen in water: 1) the classical Winkler titration, 2) electroanalytical, 3) pressure-based, and 4) optical procedures. The latter can be subdivided into numerous single methods that range from direct spectroscopy to colorimetric indicator methods. Each procedure has its inherent merits and limitations. However, in waters of high temperature, high salinities, variable pH and in the presence of other oxidants, scavenging chemicals, and biocides, the amount of dissolved oxygen is often difficult to determine due to interference. Perhaps the most frequently employed measurement approach in the oil and gas sector involves the use of membrane electrodes such as Orbisphere sensors. Such electrodes measure dissolved oxygen, but this assay is usually conducted offline. A galvanic probe is typically used online. Galvanic probes can detect oxygen, but they are not specific for oxygen and can respond to other oxidants. Essentially, galvanic probes are considered event markers and used in the oilfield if dissolved oxygen is thought to be present in flow lines or pipelines. Interferences, particularly under harsh conditions, can be a factor in over- or under-dosing with desired treatment chemicals (e.g., scavengers, corrosion inhibitors). Elevated temperatures and the presence of hydrocarbons often necessitate offline measurements that substantially increase the prospects for oxygen contamination in the samples.

While there are many methods for oxygen measurements, such determinations are often challenging in waters that have competing oxidants, high temperatures, variable pH values, hydrocarbons, or elevated salinities. Extremes of such characteristics are associated with interferences and sometimes demand offline monitoring prior to a decision on how to respond to these situations. Often the chemical nature of the oxidant being measured is less than entirely certain.

The SERS device 100 may be used in situ for the real-time detection and measurement in-situ of dissolved oxygen, and the SERS device 100 is robust enough to withstand harsh industrial environments, constituting a significant technological advance. As a spectroscopic method in visible light range, Raman detectors can distinguish between oxygen and other potentially interfering chemicals in both vapor form and aqueous solution form. The main technical challenge of prior Raman methods is the low limit of detection. The SERS device 100 improves the sensitivity substantially to a practical level. In addition, the SERS device 100 offers other advantages: 1) the lack of oxygen consumption during assay, 2) good precision and accuracy characteristics, 3) the ability to remote sense using optical fibers, 4) few interferences, and 5) the ability to miniaturize. The in-situ, real-time nature of the disclosed sensor allows operators to adjust to inherent levels and avoid an under or over response to the presence of oxygen. This ability will result in increased efficiency and cost effectiveness of their management efforts. Thus, in-situ monitoring aspects allow real-time data to be collected so that oxygen levels can be rapidly assessed and management decisions made in response to such measurements. The SERS device 100 may be used under a variety of conditions of temperature, pH, oxygen scavenging chemicals, and salinity regimes, and in hydrocarbon phases. The SERS device 100 may be used outside the oil and gas industry in a wide variety of other industrial sectors where oxygen measuring technology is required.

In a fourth embodiment, the SERS device 100 performs real-time detection of fugitive emissions. The fugitive emissions include light hydrocarbons and hazardous air pollutants. As noted above, traditional approaches for limiting corrosion and maintaining the integrity of the metallic infrastructure in the water, oil, and gas industry are inadequate, and traditional monitoring the impact of corrosion control measures is inadequate.

The SERS device 100 measures volatile gas-phase compounds ranging from light hydrocarbons (e.g., methane and ethane) to regulated hazardous air pollutants such as benzene, toluene, ethyl benzene, o-, m-, and p-xylenes, and hydrogen sulfide. The SERS device 100 may also detect ammonia, nitrogen oxides, and carbon monoxide to provide the ability to distinguish methane and volatile organic carbon emanating from fugitive emissions against those originating from livestock, landfills, and combustion. The SERS device 100 may be coupled with simulation modeling and prediction software to provide real-time analyses of single-point emissions (e.g., storage tanks and treatment processes) or spatially distributed to form a sensor network that will continually monitor local or regional emissions.

In other embodiments, the SERS device 100 analyzes $CO_2$; microbial-induced corrosion through detection of oxidized and reduced sulfur species; perfluoro contaminants and organotins such as perfluorooctanoic sulfonate, triphenyl tin chloride, tributyl tin chloride, dibutyl tin chloride, and monobutyl tin chloride; plastic microparticles such as polypropylene, nylon, polystyrene, polyvinyl chloride, and polyethylene; other fugitive emissions such as propane and butane; hazardous gases such as $H_2S$ and CO; other gases such as $NO_2$, $NH_4$, and $CO_2$ and whether those compounds are from fugitive emissions or other sources such as livestock, landfills, or combustion; regulated compounds such as benzene, toluene, ethyl benzene, o-xylene, m-xylene, and p-xylene; and the integrity of well casings and unintended releases along pipelines and other infrastructure.

Figure 13:
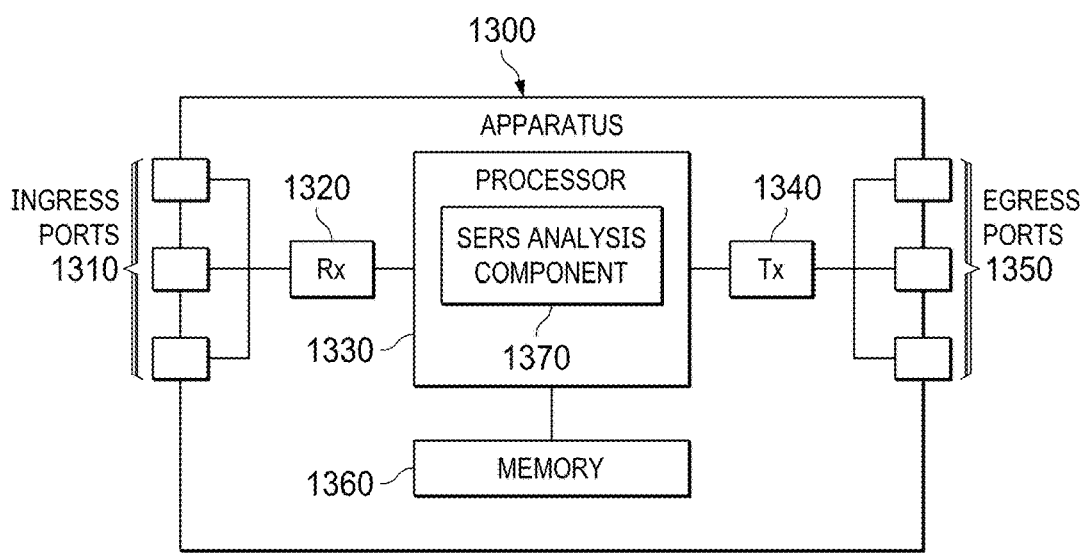
FIG. 13 is a schematic diagram of an apparatus according to an embodiment of the disclosure.

FIG. 13 is a schematic diagram of an apparatus 1300 according to an embodiment of the disclosure. The apparatus 1300 may implement the disclosed embodiments, for instance the computer 840. The apparatus 1300 comprises ingress ports 1310 and an RX 1320 or receiving means to receive data; a processor, 1330 or logic unit, baseband unit, CPU, or processing means to process the data; a TX 1340 or transmitting means and egress ports 1350 to transmit the data; and a memory 1360 or data storing means to store the data. The apparatus 1300 may also comprise OE components, EO components, or RF components coupled to the ingress ports 1310, the RX 1320, the TX 1340, and the egress ports 1350 to provide ingress or egress of optical signals, electrical signals, or RF signals.

The processor 1330 is any combination of hardware, middleware, firmware, or software. The processor 1330 comprises any combination of one or more CPU chips, cores, FPGAs, ASICs, or DSPs. The processor 1330 communicates with the ingress ports 1310, the RX 1320, the TX 1340, the egress ports 1350, and the memory 1360. The processor 1330 comprises a SERS analysis component 1370, which implements the disclosed embodiments. The inclusion of the SERS analysis component 1370 therefore provides a substantial improvement to the functionality of the apparatus 1300 and effects a transformation of the apparatus 1300 to a different state. Alternatively, the memory 1360 stores the SERS analysis component 1370 as instructions, and the processor 1330 executes those instructions.

The memory 1360 comprises any combination of disks, tape drives, or solid-state drives. The apparatus 1300 may use the memory 1360 as an over-flow data storage device to store programs when the apparatus 1300 selects those programs for execution and to store instructions and data that the apparatus 1300 reads during execution of those programs, for instance as a computer program product. The memory 1360 may be volatile or non-volatile and may be any combination of ROM, RAM, TCAM, or SRAM.

A computer program product may comprise computer-executable instructions stored on a non-transitory medium, for instance the memory 1360, that when executed by a processor, for instance the processor 1330, cause an apparatus to perform any of the embodiments.

In a first embodiment, an apparatus comprises: a photonic cavity; a substrate comprising a waveguide layer, wherein the waveguide layer comprises waveguides configured to direct light towards the photonic cavity; and a wafer bonded to the substrate to define the photonic cavity. In a second embodiment, the photonic cavity is configured to permit a fluid to flow freely into and out of the apparatus. In a third embodiment, the waveguides are arranged in a one-dimensional (1D) grid. In a fourth embodiment, the waveguides are arranged in a two-dimensional (2D) grid. In a fifth embodiment, the wafer comprises: a top side; and a nanowire array affixed to the top side. In a sixth embodiment, the nanowire array comprises nanowires, and wherein each of the nanowires is configured to serve as a surface-enhanced Raman scattering (SERS) particle. In a seventh embodiment, each of the nanowires comprises a metal coating that is superhydrophobic and configured to provide fouling resistance. In an eighth embodiment, each of the nanowires comprises a spun-coated top that is configured to create a surface-enhanced Raman scattering (SERS) hot spot. In a ninth, the nanowires are vertically aligned with each other. In a tenth embodiment, the nanowires are arranged in a two-dimensional (2D) grid. In an eleventh embodiment, the substrate and the wafer are bonded to each other via flip-chip bonding. In a twelfth embodiment, the apparatus is configured to be a surface-enhanced Raman scattering (SERS) detector.

In a thirteenth embodiment, a surface-enhanced Raman scattering (SERS) detection system comprises: a light source configured to emit an incident light; a SERS device comprising: a substrate comprising a waveguide layer configured to direct the incident light, a photonic cavity configured to permit a fluid to flow freely into and out of the SERS device, and a wafer comprising: a top side, and a nanowire array affixed to the top side, wherein the nanowire array comprises nanowires configured to serve as SERS particles; a photodetector configured to: receive scattered light from the SERS device, convert the scattered light into an electrical signal, and transmit the electrical signal; and a computer configured to analyze the electrical signal to determine whether a contaminant exists in the fluid. In a fourteenth embodiment, the computer is further configured to further analyze the electrical signal to determine a concentration of the contaminant.

In a fifteenth embodiment, a method of performing a surface-enhanced Raman scattering (SERS) analysis, the method comprises: directing, using a waveguide layer of a SERS device, an incident light towards a photonic cavity of the SERS device; permitting, using the photonic cavity, a fluid to flow freely into and out of the SERS device; causing, within the photonic cavity, an interaction among the incident light, the fluid, and a nanowire array of the SERS device to create scattered light; converting the scattered light into an electrical signal; and analyzing the electrical signal to determine whether a contaminant exists in the fluid. In a sixteenth embodiment, the method further comprises further analyzing the electrical signal to determine a concentration of the contaminant. In a seventeenth embodiment, the scattered light is inelastically scattered via a Raman effect. In an eighteenth embodiment, the fluid is oil. In a nineteenth embodiment, the fluid is water. In a twentieth embodiment, the fluid is blood. Any of the first to twentieth embodiments may be combined to form a new embodiment.

While several embodiments have been provided in the present disclosure, it may be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, components, techniques, or methods without departing from the scope of the present disclosure. Other items shown or discussed as coupled may be directly coupled or may be indirectly coupled or communicating through some interface, device, or intermediate component whether electrically, mechanically, or otherwise. Other examples of changes, substitutions, and alterations are ascertainable by one skilled in the art and may be made without departing from the spirit and scope disclosed herein.

What is claimed is:

1. An apparatus comprising:
a photonic cavity;
a substrate; and
a wafer comprising:
a top side,
a waveguide layer disposed on the top side and comprising waveguides configured to direct light towards the photonic cavity, and
a nanowire array affixed to the waveguide layer and complementing the waveguides,
wherein the substrate and the wafer are bonded to each other to define the photonic cavity between the substrate and the wafer.

2. The apparatus of claim 1, wherein the photonic cavity is configured to permit a fluid to flow freely into and out of the apparatus.

3. The apparatus of claim 1, wherein the waveguides are arranged in a one-dimensional (1D) grid.

4. The apparatus of claim 1, wherein the waveguides are arranged in a two-dimensional (2D) grid.

5. The apparatus of claim 1, wherein the nanowire array comprises nanowires, and wherein each of the nanowires is configured to serve as a surface-enhanced Raman scattering (SERS) particle.

6. The apparatus of claim 5, wherein each of the nanowires comprises a metal coating that is superhydrophobic and configured to provide fouling resistance.

7. The apparatus of claim 5, wherein each of the nanowires comprises a spun-coated top that is configured to create a surface-enhanced Raman scattering (SERS) hot spot.

8. The apparatus of claim 5, wherein the nanowires are vertically aligned with each other.

9. The apparatus of claim 5, wherein the nanowires are arranged in a two-dimensional (2D) grid.

10. The apparatus of claim 1, wherein the substrate and the wafer are bonded to each other via flip-chip bonding.

11. The apparatus of claim 1, wherein the apparatus is configured to be a surface-enhanced Raman scattering (SERS) detector.

12. A surface-enhanced Raman scattering (SERS) detection system comprising:
a light source configured to emit an incident light;
a SERS device comprising:
a substrate,
a photonic cavity configured to permit a fluid to flow freely into and out of the SERS device, and
a wafer comprising:
a top side,
a waveguide layer disposed to the top side and comprising waveguides configured to direct light towards the photonic cavity, and
a nanowire array affixed to the top side and complementing the waveguides, wherein the nanowire array comprises nanowires configured to serve as SERS particles, wherein the substrate and the wafer are bonded to each other to define the photonic cavity between the substrate and the wafer;
a photodetector configured to:
receive scattered light from the SERS device,
convert the scattered light into an electrical signal, and
transmit the electrical signal; and
a computer configured to analyze the electrical signal to determine whether a contaminant exists in the fluid.

13. The SERS detection system of claim 12, wherein the computer is further configured to further analyze the electrical signal to determine a concentration of the contaminant.

14. A method of performing a surface-enhanced Raman scattering (SERS) analysis, the method comprising:
providing a surface-enhanced Raman scattering (SERS) device comprising:
a photonic cavity;
a substrate, and
a wafer comprising:
a top side,
a waveguide layer disposed on the top side and comprising waveguides configured to direct light towards the photonic cavity, and
a nanowire array affixed to the top side and complementing the waveguides,
wherein the substrate and the wafer are bonded to each other to define the photonic cavity between the substrate and the wafer;
directing, using the waveguide layer of the SERS device, an incident light towards the photonic cavity of the SERS device;

permitting, using the photonic cavity, a fluid to flow freely into and out of the SERS device;

causing, within the photonic cavity, an interaction among the incident light, the fluid, and the nanowire array of the SERS device to create scattered light;

converting the scattered light into an electrical signal; and analyzing the electrical signal to determine whether a contaminant exists in the fluid.

15. The method of claim 14, further comprising further analyzing the electrical signal to determine a concentration of the contaminant.

16. The method of claim 14, wherein the scattered light is inelastically scattered via a Raman effect.

17. The method of claim 14, wherein the fluid is oil.

18. The method of claim 14, wherein the fluid is water.

19. The method of claim 14, wherein the fluid is blood.

20. The method of claim 14, wherein the waveguides and the nanowire array together form peaks and valleys such that tops of the valleys are located below tops of the peaks in a direction towards a bottom of the substrate.

21. The method of claim 14, further comprising preventing the fluid from passing through the substrate.

22. The method of claim 14, wherein the nanowire array and the waveguides are integrated together.

23. The apparatus of claim 1, wherein the waveguides and the nanowire array together form peaks and valleys such that tops of the valleys are located below tops of the peaks in a direction towards a bottom of the substrate.

24. The apparatus of claim 1, wherein the substrate is configured to prevent a fluid from passing through the substrate.

25. The apparatus of claim 1, wherein the nanowire array and the waveguides are integrated together.

26. The SERS detection system of claim 12, wherein the waveguides and the nanowire array together form peaks and valleys such that tops of the valleys are located below tops of the peaks in a direction towards a bottom of the substrate.

27. The SERS detection system of claim 12, wherein the substrate is configured to prevent the fluid from passing through the substrate.

28. The SERS detection system of claim 12, wherein the nanowire array and the waveguides are integrated together.

* * * * *